United States Patent [19]
Salyer

[11] Patent Number: 5,804,266
[45] Date of Patent: *Sep. 8, 1998

[54] MICROWAVABLE THERMAL ENERGY STORAGE MATERIAL

[75] Inventor: Ival O. Salyer, Dayton, Ohio

[73] Assignee: The University of Dayton, Dayton, Ohio

[*] Notice: The term of this patent shall not extend beyond the expiration date of Pat. No. 5,565,132.

[21] Appl. No.: 623,401

[22] Filed: Mar. 28, 1996

[51] Int. Cl.$^6$ .............................. C09K 3/18; F28D 17/00
[52] U.S. Cl. ...................... 428/35.2; 428/35.3; 428/35.7; 252/70; 165/10; 165/53; 524/489; 524/490; 524/497
[58] Field of Search ................................ 252/70; 165/10, 165/53; 524/489, 490, 493; 428/35.2, 35.3, 35.7

[56] References Cited

U.S. PATENT DOCUMENTS

| | | |
|---|---|---|
| 3,927,291 | 12/1975 | Peterson . |
| 4,518,651 | 5/1985 | Wolfe, Jr. . |
| 5,106,520 | 4/1992 | Salyer . |
| 5,118,747 | 6/1992 | Pollart et al. . |
| 5,282,994 | 2/1994 | Salyer . |
| 5,338,911 | 8/1994 | Brandberg et al. . |
| 5,565,132 | 10/1996 | Salyer ....................................... 252/70 |

*Primary Examiner*—Richard Weisberger
*Attorney, Agent, or Firm*—Killworth, Gottman, Hagan & Schaeff, L.L.P.

[57] ABSTRACT

A microwavable thermal energy storage material is provided which includes a mixture of a phase change material and silica, and a carbon black additive in the form of a conformable dry powder of phase change material/silica/carbon black, or solid pellets, films, fibers, moldings or strands of phase change material/high density polyethylene/ethylene-vinyl acetate/silica/carbon black which allows the phase change material to be rapidly heated in a microwave oven. The carbon black additive, which is preferably an electrically conductive carbon black, may be added in low concentrations of from 0.5 to 15% by weight, and may be used to tailor the heating times of the phase change material as desired. The microwavable thermal energy storage material can be used in food serving applications such as tableware items or pizza warmers, and in medical wraps and garments.

24 Claims, 2 Drawing Sheets

MICROWAVABLE THERMAL ENERGY STORAGE MATERIAL

GOVERNMENT RIGHTS

The Government has rights in this invention pursuant to Contract No. 19X-SC542C awarded by the U.S. Department of Energy.

BACKGROUND OF THE INVENTION

The present invention relates to a microwavable thermal energy storage material which includes a phase change material and a carbon black filler which allows the phase change material to be rapidly heated in a microwave oven.

Phase change materials are known which may be repeatedly converted between solid and liquid phases and utilize their latent heats of fusion to absorb, store and release energy to heat or cool during such phase conversions. These latent heats of fusion are greater than the sensible heat capacities of the materials. For example, in phase change materials, the amount of energy absorbed upon melting or released upon freezing is much greater than the amount of energy absorbed or released upon increasing or decreasing the temperature of the material over an increment of 10° C.

Upon melting and freezing, per unit weight, a phase change material (PCM) absorbs or releases substantially more energy than a sensible heat storage material that is heated or cooled in generally the same temperature range. In contrast to a sensible heat storage material that absorbs and releases energy essentially uniformly over a broad temperature range, a phase change material absorbs and releases a large quantity of energy in the vicinity of its melting/freezing point. However, due to its relatively high specific heat, the phase change material can supply a significant amount of sensible heat as well.

Phase change materials capable of storing and releasing thermal energy have found many applications including beverage and food containers, medical wraps, and textile applications such as garments. For example, my U.S. Pat. No. 5,106,520 discloses a thermal energy storage material in the form of a dry powder formed from an alkyl hydrocarbon phase change material and silica particles. However, when used for heating applications, the phase change material must be "charged" prior to use to melt the phase change material. This is time consuming as it may require 2 to 4 hours of direct heating to properly charge the phase change material.

It would be desirable to heat such phase change materials in a microwave oven where more rapid and uniform heating throughout could take place. However, neither the alkyl hydrocarbon phase change material nor the silica particles effectively absorb microwave energy. While the phase change material may be enhanced with microwave absorbing additives such as water, glycerine, polyethylene glycol, or clathrates which impart microwavability, such additives reduce the thermal energy storage (per unit of weight) of the phase change material/silica powder as they are not effective phase change material absorbers.

Further, while such additives provide microwave heating capability to the phase change material, a heating time of 4 to 8 minutes is still required to properly charge the phase change material. For certain applications such as food service and medical applications, it would be desirable to be able to charge the phase change material in shorter heating cycles of several minutes or less.

Accordingly, there is still a need in the art for a phase change material which may be rapidly charged in a microwave oven without reducing its thermal energy storage.

SUMMARY OF THE INVENTION

The present invention meets that need by providing a thermal energy storage material including a phase change material and a carbon black additive which enables the phase change material to be rapidly and uniformly heated in a microwave oven. The carbon black is preferably an electrical conductive carbon black which is non-toxic, inexpensive, and environmentally safe. In addition, the carbon black additive can be added at relatively low concentrations in comparison to other microwave absorbing additives, and does not reduce the thermal energy storage of the phase change material.

According to one aspect of the present invention, a microwavable thermal energy storage material is provided comprising, in combination, from about 85 to 99.5% by weight of a mixture of a phase change material (PCM) and finely divided silica particles and from about 0.5 to 15% by weight of an additive comprising carbon black which imparts microwave heating capability to the mixture. Preferably, the additive comprises electrically conductive carbon black.

The phase change material is preferably a crystalline alkyl hydrocarbon having a heat of fusion of greater than about 30 cal/g. Other phase change materials such as crystalline fatty acids, crystalline fatty acid esters, crystalline acyclic hydrocarbons and crystalline aromatic hydrocarbons may be also be used. The phase change material preferably has a melting and freezing point of from about 20°–100° C., and preferably from about 25°–90° C., and comprises from about 50–80% by weight of the PCM/silica mixture.

In this embodiment of the invention, the mixture of silica and phase change material is preferably in the form of a free-flowing, conformable powder-like mix, which may be prepared in accordance with U.S. Pat. Nos. 5,106,520 or 5,282,994, incorporated herein by reference. Preferred silicas are those having a particle size of about 0.005 to about 0.025 microns. Despite their higher cost, the silica particles preferably are hydrophobic silica particles as disclosed in U.S. Pat. No. 5,282,994, incorporated herein by reference. The preferred hydrophobic silica particles may be prepared by a fumed process or by precipitation and then surface treated with silane coupling agents (e.g., $(CH_3)_2$-Si-$Cl_2$) or silicone resins. However, normal untreated hydrophylic silicas (either fumed or precipitated) may be used where resistance to liquid water or high relative humidity is not required and lower cost silica particles are desirable.

The electrically conductive carbon black additive preferably has a particle size of about 25–35 nm and a surface area of between about 245 to 260 $m^2/gm$. The electrically conductive carbon black has an advantage over the use of non-conductive carbon black in that the carbon particles exist as long chains, which enables the particles to more effectively absorb microwave energy. Thus, the electrically conductive carbon black may be used in much smaller amounts than non-conducting carbon black. In a preferred embodiment, the electrically conductive carbon black additive comprises from about 1 to 5% by weight of the thermal energy storage material. However, when very rapid microwave heating is desired, higher concentrations in the range of 5 to 15% may be used. The thermal energy storage material may further include an amount of glycerine in the range of 1 to 10% by weight. The combination of the electrically conductive carbon black and the glycerine, both of which are microwave absorbing additives, has been found to be useful in food serving and clothing applications.

In another embodiment of the invention, a microwavable thermal energy storage material is provided comprising from about 84 to 92% by weight of a solidified melt mixture of a phase change material, a polyolefin resin, and an ethylene copolymer; and from about 8 to 16% of a combination of finely divided silica particles and an additive, wherein the additive comprises from about 0.5 to 15% by weight of the electrically conductive carbon black. The use of a solidified melt mixture in combination with the carbon black additive provides a moldable material which may be rapidly heated.

The phase change material is preferably a crystalline alkyl hydrocarbon having a melting point of from about 25°–90° C. The polyolefin resin in the melt mixture is preferably selected from the group consisting of uncrosslinked high density polyethylene and polypropylene. The ethylene copolymer is preferably an ethylene-vinyl acetate copolymer containing approximately 10–20% by weight vinyl acetate. In an alternative embodiment, the ethylene copolymer may be an ethylene-methyl acrylate or ethylene-ethyl acrylate containing 10–20% by weight acrylate.

The silica particles used in the melt mixture are preferably precipitated silica particles having particles sizes of from 0.005 to 0.025 microns. A preferred process for making the solidified melt mixture is disclosed in copending application Ser. No. 08/468,441, filed Jun. 6, 1995 and entitled THERMOPLASTIC, MOLDABLE, NON-EXUDING PHASE CHANGE MATERIALS, the disclosure of which is hereby incorporated by reference.

The present invention also provides a microwavable article comprising a liquid impervious enclosure having dispersed therein a microwavable thermal energy storage material containing a carbon black additive as described above. In one embodiment, the article comprises a medical wrap and the liquid impervious enclosure comprises a polymeric envelope. In another embodiment, the article comprises a tableware item, where the liquid impervious enclosure is a plastic housing. For example, the thermal energy storage material may be included between the walls of a food or beverage container such as cups, bowls, plates, trays, etc. The microwavable thermal energy storage material of the present invention may be used in a variety of other heating applications such as pizza warmers or clothing.

When the thermal energy storage material is heated in a microwave, the electrically conductive carbon black allows the phase change material to be heated above its melting point in less than about four minutes. However, the heating times may be tailored as desired by varying the amount of electrically conductive carbon black added to the PCM/silica mixture. This ability to tailor the heating time makes the thermal energy storage material suitable for a wide variety of applications for which previous phase change materials have not been universally adapted.

Accordingly, it is an object of the present invention to provide a microwavable thermal energy storage material comprising a mixture of a phase change material and silica particles and a carbon black additive which allows the phase change material to be rapidly heated in a microwave oven. These, and other objects and advantages of the present invention, will become apparent from the following detailed description, the accompanying drawings, and the appended claims.

DETAILED DESCRIPTION OF THE PREFERRED EMBODIMENT

Figure 1:
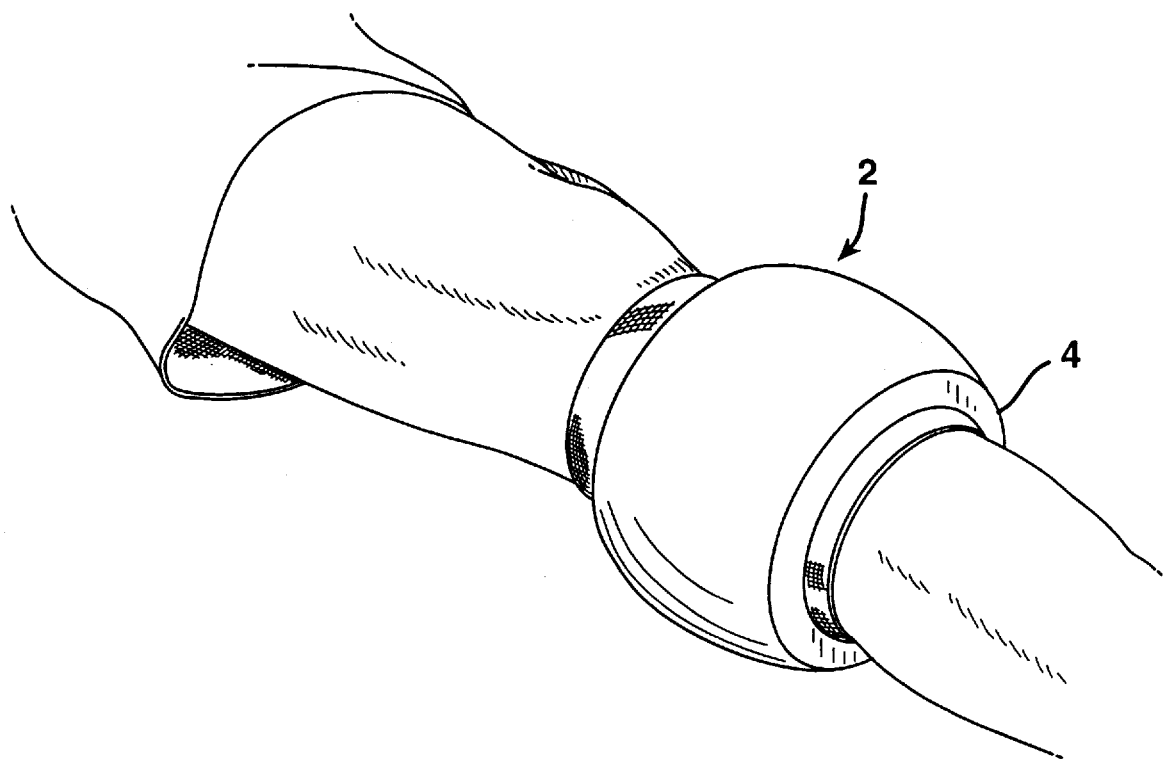
FIG. 1 is a diagrammatic view of a medical wrap utilizing the microwavable energy storage material of the present invention.

The use of carbon black as an additive in the thermal energy storage material of the present invention provides many significant and unexpected advantages over the use of other additives such as water, glycerine, polyethylene glycol or clathrates. While conventional carbon blacks are suitable for use in the present invention, electrically conductive carbon blacks are preferable as they have a larger particle size than most non-conducting carbon blacks and the carbon particles exist as long chains, which contributes to their electrical conductivity. Further, the electrically conductive carbon black contains reactive groups which absorb large amounts of energy in the microwave region of the spectrum. Conventional non-conductive carbon blacks do not contain long particle chains, and do not absorb microwave energy as effectively. As a result, large amounts of conventional carbon black would be required to provide the same microwavability as a smaller amount of electrically conducting carbon black. The electrically conductive carbon black, however, may be used in low concentrations, and allows the phase change material to be microwave heated in four minutes or less, which is much faster than with the addition of other additives.

The electrically conductive carbon black has the additional advantage that it absorbs the phase change material to approximately the same degree as the silica particles, and thus does not reduce the thermal storage (per unit of weight) as do other additives such as glycerine or water. Glycerine and water are liquids that do not absorb the alkyl hydrocarbon PCM. Thus, more silica has to be added in order to preserve the conformability and free-flowing characteristic of the product. This results in compositions that have a lower total percentage of PCM and thus less thermal energy storage. Since the electrically conducting carbon blacks are solid particles that adsorb the PCM to about the same degree as silica, the carbon black can be substituted for an equal weight of silica in the total dry powder formulation. Thus, the thermal storage of the conformable dry powder containing the electrically conducting carbon black is substantially equal to the same formulation without the carbon black.

The preferred electrically conductive carbon black for use in the present invention is available from Cabot Corp. under the designation Vulcan® XC72R, and has a particle size of 30 nm and a surface area of 254 $m^2$/gm. The carbon black is preferably used in fluffy form when a dry powder phase change material mixture is used. In embodiments where the phase change material is in the form of a solidified melt mixture, the pelletized form (Vulcan® XC72) is preferred. While a disadvantage of the use of carbon black is that the energy storage material is of a black color, in most applications, the dry powder/solidified melt mixture will be completely enclosed, so it will not be visible. In applications where the powder or melt mixture is enclosed in a film package, the film may be opaque.

The preferred phase change material for use in the present invention is a linear crystalline alkyl hydrocarbon having a carbon chain of length of $C_{14}$ or greater. A number of commercially available waxes are useful as phase change materials in the present invention including Shellwax® 300, (MP 60°–65° C.), available from Shell Oil Co. Other suitable PCMs include Shellwax® 100 (MP 42°–44° C.), Shellwax® 200 (MP 52°–55° C.) and Shellwax® 400 (MP 73°–78° C.).

The silica particles used with the dry powder phase change material mixture are preferably surface treated with about 15 pph of a silane coupling agent such as dimethyldichlorosilane or silicone resin to make them hydrophobic. The use of a hydrophobic silica is important as it prevents phase separation of the PCM and silica in the event the dry powder mixture is exposed to liquid water or high humidity at a temperature which is above the melting point of the PCM. A preferred surface-modified silica is available from PPG Industries under the designation BXS-303. Other suitable silicas include BXS-310 and BXS-320 (PPG), TS 610 and TS 720, available from Cabot Corporation, and comparable products from DeGussa.

In the solidifed melt mix, the problem of phase separation, noted when PCM/silica dry powders are exposed to liquid water, is absent. Accordingly, the lower cost hydrophylic ABS precipitated silica from PPG Industries may be used for most applications. ABS is a normal hydrophylic silica with a surface area of 150 $m^2$/gram and a particle size of about 0.22 microns.

Where the phase change material is in the form of a dry powder, the microwavable thermal energy storage material is preferably formed by heating the alkyl hydrocarbon phase change material, stirring in the carbon black and mixing, and then adding silica particles into the mixture incrementally until a dry powder is formed. Alternatively, the carbon black may be incorporated into the phase change material simultaneously with the addition of the silica particles.

The thermal energy storage material may also be enhanced by the inclusion of an antioxidant in the formulation. When used, the antioxidants should be added in an amount of from 0.1 to 10% by weight and preferably 0.5 to 2.0 by weight based on the weight of the phase change material. Exemplary antioxidants include the well-known hindered phenol material and aromatic amines. Preferred antioxidants include BHT (butylated hydroxy toluene) available from Eastman Chemical Co., and Santowhite powder (i.e., 4,4'-isopropylidene bis(6-tert-butyl-m-cresol), available from Monsanto Co.

Further, the thermal stability of the PCM/silica dry powder and the solidified melt mix to repeated heating or overheating is significantly enhanced if residual air in the liquid impervious container is replaced with $CO_2$ or nitrogen.

The resulting thermal energy storage material may be incorporated into a number of articles including food serving trays, medical wraps, or clothing. FIG. 1 illustrates a medical wrap 2, specifically a knee joint wrap comprising an outer envelope 4, formed from a hydrocarbon liquid impervious polymer such as a butadiene-acrylonitrile copolymer, a polyester, 4-methylpentene-1, polyethylene terephthalate, a Nylon such as Nylon 6 or Nylon 66, a vinyl polymer such as plasticized polyvinyl chloride, plasticized polyvinylidene chloride, low and high density polyethylene, or ethylene vinyl-acetate copolymers. Housed within the liquid impervious outer envelope may be a powder-like mix comprising the PCM, silica and carbon black. Alternatively, the envelope may be filled with the solidified melt mixture and carbon black.

Figure 2:
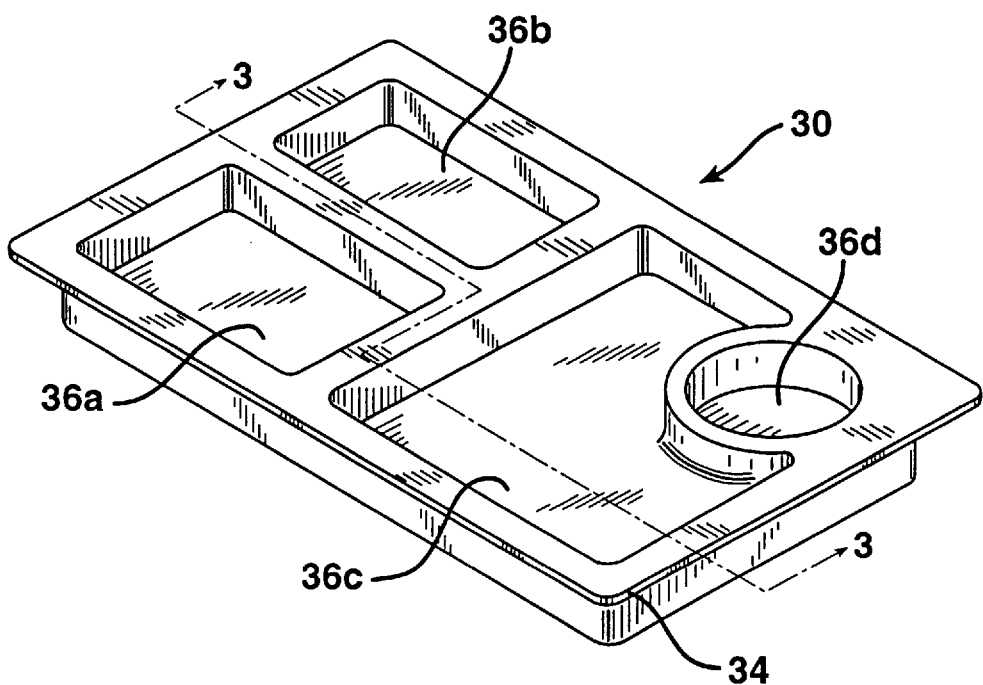
FIG. 2 is a diagrammatic view of a serving tray utilizing the microwavable energy storage material of the present invention.
Figure 3:
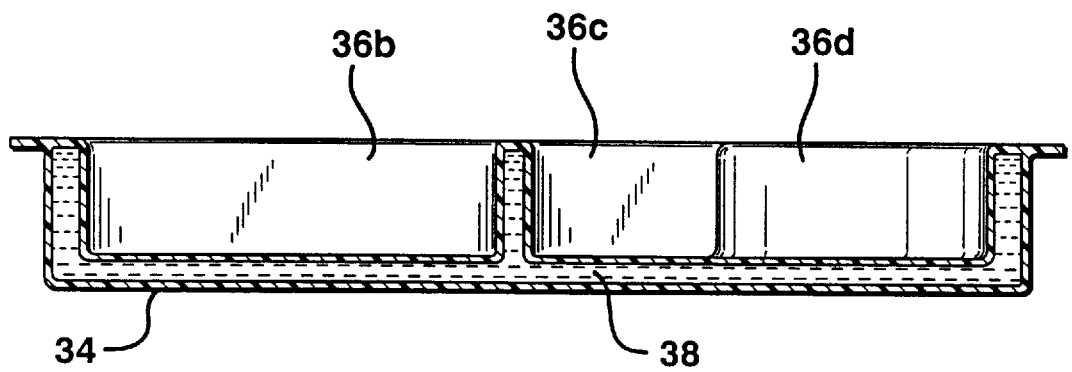
FIG. 3 is a sectional view taken along lines 5—5 in FIG. 3.

FIGS. 2 and 3 depict a tableware item such as a dinner serving tray of the type used by airlines, etc. which incorporates the microwavable thermal energy storage material therein. The tray comprises a plurality of compartments 36a–d which act as receptacles for food and a beverage container. Here, serving tray 30 comprising a plastic housing 34 which is filled with the mixture 38 of PCM, silica and conductive carbon black. Alternatively, the tray may be filled with the solidified melt mixture and conductive carbon black, which is molded and shaped to fit the spaces between the walls of the housing.

The microwavable thermal energy storage material may be used in a number of other applications including clothing which is designed to release heat to the wearer at a desired temperature, or in pizza warmers which are designed to keep pizzas warm during the period of time in which the pizza is being delivered to a consumer.

It should be appreciated that by varying the concentration of the carbon black, the microwave heating time can be varied over a wide range of times to provide the desired heating time. For example, where the energy storage material comprises 15% by weight conductive carbon black, heating times as short as 15–30 seconds may be achieved, while the use of 1% by weight conductive carbon black may be used to achieve a heating time of about 4 minutes.

In order that the invention may be more readily understood, reference is made to the following examples, which are intended to be illustrative of the invention, but are not intended to be limiting in scope.

EXAMPLE 1

A microwavable thermal energy storage material was prepared in accordance with the present invention by placing 100 grams of Shellwax® 100 onto a mixing tray. About 0.1 gm of BHT antioxidant from Eastman Chemical Company was added. The mixture was heated on the mixing tray to about 90° C. About 1% by weight Vulcan® XC72R electrically conductive carbon black additive was added incrementally to the mixture. BXS-320 (PPG Industries) silica was then incrementally added to the mixture to obtain a dry powder at a total additive level of about 30–35 weight percent.

The procedure was repeated, but using 1.5% by weight and 2.5% by weight of the Vulcan® XC72R carbon black.

The three samples obtained were tested for microwave heating (using a high setting) and the results are shown below in Table I.

TABLE 1

| Sample | Microwave Heating Time | | | |
| --- | --- | --- | --- | --- |
| | 2 min. | 4 min. | 6 min. | 8 min. |
| 1% carbon black | 49° C. | 79° C. | 101° C. | 107° C. |
| 1.5% carbon black | 53° C. | 89° C. | 110° C. | 127° C. |
| 2.5% carbon black | 140° C. | fumes | — | — |

As can be seen, the level of electrically conductive carbon black can be varied to obtain the desired heating time.

EXAMPLE 2

A microwavable thermal energy storage material was prepared by placing 100 gm of Shellwax® 300 in a mixing tray on a hot plate. 1.0 gm of BHT antioxidant was added and the mixture was heated to about 100° C. 1.5 grams of Vulcan® XC72R carbon black was then added to the mixture. BXS-320 silica was then incrementally added to the mixture to obtain a dry powder at 65:35 ratio of PCM/BHT:silica/carbon black composition. The sample was then microwave heated and the results are shown below in Table 2.

TABLE 2

| Sample | Microwave Heating Time | | | | |
|---|---|---|---|---|---|
| | 15 sec. | 30 sec. | 1 min. | 2 min. | 4 min. |
| 1.5% Carbon black | 49° C. | 50° C. | 60° C. | 85° C. | 122° C. |

EXAMPLE 3

A microwavable thermal energy storage material was prepared by placing 1000 gm of Shellwax® 300 in a mixing tray on a hot plate. 500 gm of BXS-303 silica and 88.24 gm of Vulcan® XC72R were separately mixed. 10 grams BHT antioxidant was added to the PCM and heated to about 100° C. The mixed silica and carbon black were then added to the PCM/BHT mixture to obtain a gel and then a dry powder. The composition of the powder was 65:35 ratio of PCM/BHT:silica/carbon black. 50 grams of the powder was removed and tested for microwave heating. The results are shown below in Table 3.

TABLE 3

| Sample | Microwave Heating Time | | | |
|---|---|---|---|---|
| | 15 sec. | 30 sec. | 45 sec. | 60 sec. |
| 5.5% Carbon black | 52° C. | 77° C. | 90° C. | 140° C.-fumes |

The thermal energy storage properties of the sample were also analyzed by Differential Scanning Calorimetry (DSC), and the results are shown below in Table 4.

TABLE 4

| Run No. | Tm (°C.) | Tc (°C.) | Tm − Tc (°C.) | Heat of Fusion (Cal/g.) | Heat of Recryst. (Cal/g.) |
|---|---|---|---|---|---|
| 1 | 70.66 | 57.82 | 12.84 | 30.80 | 29.84 |
| 2 | 70.66 | 57.55 | 13.11 | 31.66 | 30.25 |
| Avg. | 70.66 | 57.685 | 21.975 | 31.23 | 30.045 |

The DSC analysis shows that the thermal storage of the dry powder containing 15% Vulcan® XC72R is equivalent to dry powders made with Shellwax® 300 and BXS-303 silica alone. This result also demonstrates the advantage of using electrically conducting carbon black over glycerine, water and other microwave absorbing materials which reduce thermal energy storage on a weight basis in proportion to the amount of the type of additive used in the formulation.

EXAMPLE 4

In an alternative embodiment of the invention, a thermal energy storage material was formed in the form of melt mixed solid pellets, sheets, moldings, etc. that store and release thermal energy and can also be heated with microwave energy. The thermal energy storage material was comprised of a PCM, antioxidant, a high density polyethylene (HDPE), ethylene vinyl acetate copolymer (E-VA 83/17), silica (hydrophobic BXS-303 or hydrophylic ABS), and electrical conducting carbon black (Vulcan XC72R). Although the exact proportions may be varied, one example is a composition having a ratio of 60/1/16/8/14/1 parts by weight PCM/antioxidant/HDPE/EVA/silica/carbon black. A composition of this type was prepared as follows: 60 parts of Parvan 147 (an alkyl hydrocarbon PCM having a melting temperature of 147° F.) (from Exxon) was placed in a mixing tray on an electrically heated hot plate. One part Santowhite powder antioxidant from Monsanto Co. was added, and the mixture was heated to 150° C. with stirring to melt the Parvan 147 and dissolve the antioxidant. Two separate mechanical mixtures were prepared. In one, 15 parts of ABS silica (PPG) and 1 part carbon black (Vulcan XC72R from Cabot Corp.) were mechanically mixed (to break up any lumps of the silica or carbon black) to produce a uniform gray powder. A second premix was prepared by adding 16 parts of Marlex 6006 HDPE (from Phillips Chemical Co.) and 8 parts of ethylene vinyl acetate copolymer (83/17) to produce a mixture of pellets. The premix of ABS silica/Vulcan XC72R (15/1) was incrementally added to the liquid melt (150° C.) of the Parvan 147/Santowhite Powder, with stirring, to produce a uniform black gel. The mixture of Marlex 6006/E-VA pellets was then incrementally added to the gel, with vigorous mixing, to produce a very stiff viscous black gel. The viscous gel was then poured (trowelled) into a metal mold, and a metal top plate was applied to press the gel out to form a sheet of the desired thickness.

Where pellets were desired, the top plate was removed while still hot to the touch, and the hot sheet scored with a sharp knife to produce pellets. The pellets (100 gm sample) were placed in a microwave (1000 watt) oven and found to heat to greater than 80° C. in 2 minutes and to greater than 100° C. in 4 minutes.

The melt mix as prepared above can be extruded, in a continuous process, to form sheets, films, strands or fibers. The strands can be chopped to form pellets of any desired size. The extruded pellet products may be used "as is" for certain thermal energy storage applications, or injection molded into objects of desired size and shape (e.g., moldings to fit into the empty core space of hollow core concrete blocks). The time required for the microwave heating can be controlled directly by the concentration of the conducting carbon black in the composition.

Following the above laboratory procedure, much larger lots of the microwavable melt mix compositions were then prepared in plant production equipment. The tests were conducted with a melt mix of Parvan 147/Santowhite powder/HDPE/EVA/ABS silica/XC72R (60/1/16/8/14/1) using identical weights of 5 oz., and the results are shown below in Table 5.

TABLE 5

| Carbon black (weight %) | Microwave Heating Time (Seconds) | Temperature (°C.) |
|---|---|---|
| 1 | 90 | 66–71 |
| 1.5 | 90 | 82–110 |
| 2 | 90 | 110–121 |
| 3 | 90 | 116–127 |
| 3 | 180 | 149–368 |

If a microwave heating time of a few seconds is desired for special applications, this can be achieved by increasing the conductive carbon black concentration to higher levels in the range of 5 to 15% by weight. It should be appreciated by those skilled in the art that the proportions of the individual components can be varied with some defined limits without losing the benefit of processability of microwave heating capability.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A microwavable thermal energy storage material comprising, in combination:
   a) from about 85 to 99.5% by weight of a mixture of a phase change material and finely divided silica particles; and
   b) from about 0.5 to 15% by weight of an additive comprising carbon black which imparts microwave heating capability to said thermal energy storage material.

2. The microwavable thermal energy storage material of claim 1 in which said carbon black is an electrically conductive carbon black.

3. The microwavable thermal energy storage material of claim 2 comprising from about 1 to 5% by weight of said carbon black.

4. The microwavable thermal energy storage material of claim 2 further including glycerine.

5. The microwavable thermal energy storage material of claim 2 in which said carbon black has a particle size of about 25–35 nm and a surface area of between about 245 to 260 $m^2/gm$.

6. The microwavable thermal energy storage material of claim 1 in which said silica particles have particle sizes of about 0.005 to 0.025 microns.

7. The microwavable thermal energy storage material of claim 1 in which said silica particles comprise hydrophobic silica particles.

8. The microwavable thermal energy storage material of claim 1 in which said silica particles comprise hydrophylic silica particles.

9. The microwavable thermal energy storage material of claim 1 in which said phase change material is a crystalline alkyl hydrocarbon having a melting point of from about 20°–100° C.

10. The microwavable thermal energy storage material of claim 1 in which said phase change material comprises from 50–80% by weight of said mixture.

11. A microwavable article comprising a liquid impervious enclosure having disposed therein a microwavable thermal energy storage material comprising from about 90 to 99.5% by weight of a mixture of a crystalline alkyl hydrocarbon phase change material and finely divided silica particles, and from about 0.5 to 15% by weight of an additive comprising electrically conductive carbon black which imparts microwave heating capability to said thermal energy storage material such that said phase change material disposed in said article may be microwave heated above its melting point in less than four minutes.

12. The article of claim 11 wherein residual air present in said liquid impervious enclosure is replaced with $CO_2$ or nitrogen to enhance thermal stability.

13. The article of claim 11 in which said liquid impervious enclosure is a polymeric envelope and said article comprises a medical wrap.

14. The article of claim 11 in which said liquid impervious enclosure is a plastic housing and said article comprises a tableware item.

15. A microwavable thermal energy storage material comprising, in combination:
   a) from about 85 to 99.5% by weight of a mixture of a phase change material and finely divided silica particles, said phase change material comprising a crystalline alkyl hydrocarbon; and
   b) from about 0.5 to 15% by weight of an additive which imparts microwave heating capability to said mixture such that said phase change material may be heated above its melting point in less than four minutes.

16. A microwavable thermal energy storage material comprising, in combination:
   a) from about 84 to 92% by weight of a solidified melt mixture of a phase change material, a polyolefin resin, an ethylene copolymer; and
   b) from about 8–16% by weight of a combination of finely divided silica particles and an additive, wherein said additive comprises from about 0.5 to 15% by weight of a carbon black which imparts microwave heating capability to said thermal energy storage material.

17. The microwavable thermal energy storage material of claim 16 wherein said carbon black is an electrically conductive carbon black.

18. The microwavable thermal energy storage material of claim 17 comprising from about 1 to 5% by weight of said carbon black.

19. The microwavable thermal energy storage material of claim 17 in which said carbon black has a particle size of about 25–35 nm and a surface area of between about 245 to 260 $m^2/gm$.

20. The microwavable thermal energy storage material of claim 16 wherein said polyolefin resin is selected from the group consisting of uncrosslinked high density polyethylene and polypropylene.

21. The microwavable thermal energy storage material of claim 16 wherein said ethylene copolymer is an ethylene-vinyl acetate copolymer containing approximately 10–20% by weight vinyl acetate.

22. The microwavable thermal energy storage material of claim 16 wherein said ethylene copolymer is an ethylene-methyl acrylate or. ethylene-ethyl acrylate containing 10–20% by weight acrylate.

23. The microwavable thermal energy storage material of claim 16 wherein said silica particles are precipitated silica particles having particle sizes of from 0.005 to 0.025 microns.

24. The microwavable thermal energy storage material of claim 16 wherein said phase change material is a crystalline alkyl hydrocarbon having a melting point of from about 20°–100° C.

* * * * *